United States Patent

Hofer et al.

[11] 3,989,525
[45] Nov. 2, 1976

[54] N-ISOPROPYL-2-CHLOROETHANE-(THIONO)-PHOSPHONIC ACID ESTER AMIDE COMPOUNDS AND HERBICIDAL COMPOSITIONS

[75] Inventors: Wolfgang Hofer, Wuppertal; Klaus Lürssen, Gross-Koenigsdorf, both of Germany

[73] Assignee: Bayer Aktiengesellschaft, Leverkusen, Germany

[22] Filed: Mar. 31, 1975

[21] Appl. No.: 563,760

[30] Foreign Application Priority Data
Apr. 27, 1974  Germany............ 2420627

[52] U.S. Cl. ................ 71/86; 71/87; 260/933; 260/545 P
[51] Int. Cl.[2] ........ A01N 9/36; C07F 9/24
[58] Field of Search ........ 260/933, 545 P; 71/86, 71/87

[56] References Cited
UNITED STATES PATENTS
3,787,486  1/1974  Randall et al. ............ 260/545 P

*Primary Examiner* — Anton H. Sutto
*Attorney, Agent, or Firm* — Burgess, Dinklage & Sprung

[57] ABSTRACT

New N-isopropyl-2-chloroethane-(thiono)-phosphonic acid ester amides of the general formula:

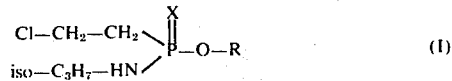

(I)

wherein
X is oxygen or sulfur, and
R is acetyl or a group of the formula

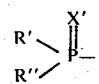

wherein
X' is oxygen or sulfur,
R' is alkoxy with 1 to 4 carbon atoms or 2-chloroethyl, and
R'' is alkoxy or alkylamino, each with 1 to 4 carbon atoms, or an $NH_2$—group; and
are outstandingly effective as plant growth regulating agents.

22 Claims, No Drawings

N-ISOPROPYL-2-CHLOROETHANE-(THIONO)-PHOSPHONIC ACID ESTER AMIDE COMPOUNDS AND HERBICIDAL COMPOSITIONS

The present invention relates to certain new N-isopropyl-2-chloroethane-(thiono)-phosphonic acid ester amide compounds and to plant-growth regulant compositions and uses thereof.

It has already been disclosed that 2-chloroethanephosphonic acid exhibits plant growth-regulating properties (see published Netherlands Patent Application No. 68/02,633). However, the activity of this compound is not always entirely satisfactory, especially if low amounts and low concentrations are used.

The present invention provides, as new compounds, the N-isopropyl-2-chloroethane-(thiono)-phosphonic acid ester amides of the general formula:

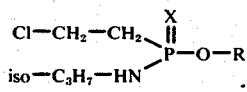  (I)

wherein
X is oxygen or sulphur, and
R is acetyl or a group of the formula

wherein
X' is oxygen or sulphur,
R' is alkoxy with 1 to 4 carbon atoms or 2-chloroethyl, and
R'' is alkoxy or alkylamino, each with 1 to 4 carbon atoms, or an NH$_2$— group.

The compounds of this invention have been found to exhibit strong plant growth-regulating properties.

Surprisingly, the N-isopropyl-2-chloroethane-(thiono)-phosphonic acid ester amides according to the invention exhibit a substantially greater plant-growth-regulating action than 2-chloroethanephosphonic acid, known from the state of the art, which is chemically the nearest active compound of the same type of action. A point to be singled out above all is that the compounds according to the invention are substantially more suitable for inhibiting vegetative plant growth than is 2-chloroethanephosphonic acid. The compounds according to the invention thus represent a valuable enrichment of the art.

Preferably R is acetyl or the

group, wherein
X' is oxygen or sulfur,
R' is a 2-chloroethyl radical or straight-chain or branched alkoxy with 1 to 3 carbon atoms (methoxy, ethoxy and propoxy should be mentioned specifically in this context) and
R'' is an amino group, or straight-chain or branched alkoxy or alkylamino, each with 1 to 3 carbon atoms (preferred radicals being, in particular, methoxy, ethoxy, monomethylamino, monoethylamino, mono-n-propylamino and mono-isopropylamino).

This invention also provides a process for the preparation of an N-isopropyl-2-chloroethane-(thiono)-phosphonic acid ester amide of the formula (I), in which an N-isopropyl-2-chloroethane-(thiono)-phosphonic acid amide halide of the general formula:

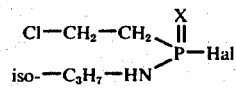  (II), wherein
X has the above-mentioned meaning, and
Hal is halogen, preferably chlorine,
is reacted with a compound of the general formula:

  III wherein
R has the above-mentioned meaning, and
Y is hydrogen or one equivalent of an alkali metal, alkaline earth metal or ammonium,
if appropriate in the presence of an acid acceptor and if appropriate in the presence of a solvent or diluent.

If N-iso-propyl-2-chloroethanephosphonic acid amide chloride and sodium acetate are used as starting materials, the course of the reaction can be represented by the following equation:

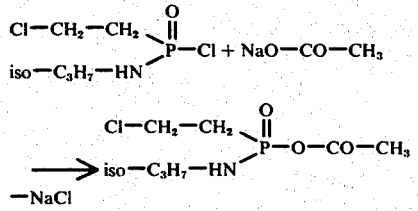

The N-isopropyl-2-chloroethane-(thiono)-phosphonic acid amide halides of the formula (II) which can be used according to the invention are either already known or can be prepared according to generally customary processes (see German Offenlegungsschrift (German Published Specification) 1,950,099).

The following may be mentioned as examples of the compounds of the formula (II) which can be used according to the invention: N-isopropyl-2-chloroethanephosphonic acid amide chloride and N-isopropyl-2-chloroethane-thiono-phosphonic acid amide chloride.

In the formula (III), Y preferably represents hydrogen, sodium, potassium, calcium or ammonium. The compounds of the formula (III) which can be used according to the invention are known and can be prepared in accordance with generally customary methods, in most cases also on an industrial scale (see Belgian Patent Specification No. 756,981).

The following may be mentioned as examples of the compounds of the formula (III) which can be used according to the invention: acetic acid, sodium acetate and potassium acetate, and also O,O-dimethylphosphric acid diester, O,O-diethylphosphoric acid diester, O,O-di-n-propylphosphoric acid diester, O,O-di-isopropyl-phosphoric acid diester, O-ethyl-O-n-propyl-phosphoric acid diester, O-ethyl-O-isopropyl-phosphoric acid diester, O-methyl-N-methyl-phosphoric acid ester amide, O-methyl-N-ethyl-phoshoric acid ester amide, O-ethyl-N-methyl-phosphoric acid ester amide, O-ethyl-N-ethyl-phosphoric acid ester amide, O-n-propyl-N-methyl-phosphoric acid ester amide, O-n-propyl-N-ethyl-phosphoric acid ester amide, O-isopropyl-N-methyl-phosphoric acid ester amide, O-isopropyl-N-iso-propyl-phosphoric acid ester amide, O-methyl-N-isopropyl-phosphoric acid ester amide, O-ethyl-N-isopropyl-phosphoric acid ester amide, O-methyl-phosphoric acid ester amide, O-ethyl-phosphoric acid ester amide, O-n-propylphosphoric acid ester amide, O-isopropyl-phoshoric acid ester amide, N-methyl-2-chloroethane-phosphonic acid amide, N-ethyl-2-chloroethane-phosphonic acid amide, N-n-propyl-2-chloroethanephosphonic acid amide, N-isopropyl-2-chloroethane-phosphonic acid amide, as well as the sodium, potassium, ammonium and calcium salts of the above-mentioned compounds, and the corresponding thiono compounds.

The process according to the invention for the preparation of the new N-isopropyl-2-chloroethane-(thiono)-phosphonic acid ester amides of the formula (I) is preferably carried out in the presence of a suitable solvent or diluent. Practically all inert organic solvents can be used for this purpose, especially aliphatic and aromatic hydrocarbons, such as petroleum ether, benzine, benzene, toluene and xylene; chlorinated aliphatic and aromatic hydrocarbons, such as methylene chloride, chloroform, carbon tetrachloride and chlorobenzene; ethers, such as diethyl ether, dibutyl ether and dioxan; ketones, such as acetone, methyl ethyl ketone, methyl isopropyl ketone and methyl isobutyl ketone; and nitriles, such as acetonitrile and propionitrile.

All customary acid-binding agents can be used as acid acceptors in carrying out the process according to the invention. Amongst these there should be mentioned especially alkali metal carbonates, such as potassium carbonate and sodium carbonate, alkali metal alcoholates, such as sodium ethylate and sodium methylate, and aliphatic, aromatic or heterocyclic amines, such as, for example, triethylamine, trimethylamine, dimethylaniline, dimethylbenzylamine and pyridine.

The reaction temperatures can be varied over a fairly wide range. In general, the reaction is carried out at between 0° and 100° C, preferably between 10° and 70° C. The reaction according to the invention is generally carried out under normal pressure.

In carrying out the process according to the invention for the preparation of the compounds of the formula (I), preferably 1 mole of a compound of the formula (III) is employed per mole of N-isopropyl-2-chloroethane-(thiono)-phosphonic acid amide halide of the formula (II). However, it is also possible to use one or other reactant in excess, although the yield is not significantly improved thereby.

In general, the reaction products of the formula (I) are isolated by, if appropriate, filtering off the crystalline precipitate produced during the reaction after the latter has been completed, adding water to the filtrate and extracting the resulting mixture repeatedly with a water-insoluble organic solvent. After drying under reduced pressure, the combined organic phases are concentrated. In some cases, working up by an aqueous method is superfluous. In that case, the procedure followed is first to filter off the precipitate which has formed during the reaction and then to concentrate the filtrate under reduced pressure.

The compounds of the formula (I) which can be prepared according to the invention are in most cases obtained, after working up, in the form of oils which cannot be distilled without decomposition. However, purification is possible by freeing the oily products from the last volatile constituents by so-called "slight distillation", that is to say by prolonged heating under reduced pressure to moderately elevated temperatures. The refractive index is used to characterize the compounds which are obtained as oils even after purification. Some compounds, however, are obtained in a crystalline form; they can be characterized as pure substances by their sharp melting point.

A particular embodiment of the process according to the invention is employed when preparing symmetrical compounds of the formula (I) which are derived from pyrophosphonic acid. In these cases it is not necessary to react the starting compound of the formula (II) with the corresponding hydroxy compound of the formula (III) or a salt of this hydroxy compound. Instead, the procedure followed is to treat the N-isopropyl-2-chloroethane-(thiono)-phosphonic acid amide halide in question, in a solvent or diluent, for one or more hours at a temperature of between 0° and 100° C with a mixture of an acid acceptor such as pyridine, water and an organic solvent such as methylene chloride. Working up is effected by extracting the reaction mixture repeatedly with dilute hydrochloric acid, subsequently drying the organic phase and concentrating it under reduced pressure.

The following may be mentioned as examples of the N-isopropyl-2-chloroethane-(thiono)-phosphonic acid ester amides of the formula (I): O-acetyl-N-isopropyl-2-chloroethane-phosphonic acid ester amide, O-acetyl-N-isopropyl-2-chloroethane-thiono-phosphonic acid ester amide, O-(O,O-dimethylphosphoryl)-N-isopropyl-2-chloroethane-phosphonic acid ester amide, O-(O,O-diethylphosphoryl)-N-isopropyl-2-chloroethane-phosphonic acid ester amide, O-(O,O-di-n-propylphosphoryl)-N-isopropyl-2-chloroethane-phosphonic acid ester amide, O-(O,O-di-isopropylphoshoryl)-N-isopropyl-2-chloroethane-phosphonic acid ester amide, O-(O-ethyl-O-n-propyl-phosphoryl)-N-isopropyl-2-chloroethane-phosphonic acid ester amide, O-(O-ethyl-O-isopropylphosphoryl)-N-isopropyl-2-chloroethane-phosphonic acid ester amide, O-(O,O-cimetylthionophosphoryl)-N-isopropyl-2-chloroethane-phosphonic acid ester amide, O-(O,O-diethyl-thionophosphoryl)-N-isopropyl-2-chloroethane-phosphonic acid ester amide, O-(O,O-di-propylthionophosphoryl)-N-isopropyl-2-chloroethane-phosphonic acid ester amide, O-(O,O-di-isopropyl-thionophosphoryl)-isopropyl-2-chloroethane-phosphonic acid ester amide, O-(O-methyl-N-methylamidophosphoryl)-N-isopropyl-2-chloroethanephosphonic acid ester amide, O-(O-methyl-N-ethyl-amidophosphoryl)-N-isopropyl-2-chloroethane-phosphonic acid ester amide, O-(O-ethyl-N-methyl-amidophosphoryl)N-isopropyl-2-chloroethane-phosphonic acid ester amide, O-(O-ethyl-N-ethylamidophosphoryl)-N-isopropyl-2-chloroethane-phosphonic acid ester amide, O-(O-n-propyl-N-ethyl-amidophosphoryl)-N-isopropyl-2-chloroethanephosphonic acid ester amide, O-(O-isopropyl-N-methylamidophosphoryl)-N-isopropyl)2-chloroethane-phosphonic acid ester amide, O-(O-n-propyl-N-ethyl-amidophosphoryl)-N-isopropyl-2-chloroethane-phosphonic acid ester amide, O-(O-isopropyl-N-isopropylamidophosphoryl)-N-isopropyl-2-chloroethanephosphonic acid ester amide, O-(O-methyl-N-isopropyl-amidophosphoryl)-isopropyl-2-chloroethane-phosphonic acid ester amide, O(O-ethyl-N-isopropylamidophosphoryl-N-isopropyl-2-chloroethane-phosphonic acid ester amide, O-(O-methyl-N-methyl-amidothionophosphoryl)-N-isopropyl-2-chloroethane-phosphonic acid ester amide, O-(O-methyl-N-ethylamidothionophosphoryl)-N-isopropyl-2-chloroethane-phosphonic acid ester amide, O-(O-ethyl-N-methyl-amidothionophosphoryl)-N-isopropyl-2-chloroethane-phosphonic acid ester amide, O-(O-ethyl-N-ethyl-amidothionophosphoryl)-N-isopropyl-2-chloroethane-phosphonic acid ester amide, O-(O-methyl-amidophosphoryl)-N-isopropyl- 2-chloroethane-phosphonic acid ester amide, O(O-ethyl-amidophosphoryl)-N-isopropyl-2-chloroethane-phosphonic acid ester amide, O-(O-n-propyl-amidophosphoryl)-N-isopropyl-2-chloroethane-phosphonic acid ester amide, O-(O-isopropyl-amidophosphoryl)-N-isopropyl-2-chloroethane-phosphonic acid ester amide, O-(O-methyl-amidothionophosphoryl)-N-isopropyl-2-chloroethane-phosphonic acid ester amide, O-(O-ethyl-amidothionophosphoryl)-N-isopropyl-2-chloroethane-phosphonic acid ester amide, O-(O-n-propyl-amidothionophosphoryl)-N-isopropyl-2-chloroethane-phosphonic acid ester amide, O-(O-isopropyl-amidothionophosphoryl)-N-isopropyl-2-chloroethane-phosphoric acid ester amide, P,P'-diisopropylamino-di-2-chloroethane-pyrophosphonic acid diamide and P,P'-diisopropylamino-di-2-chloroethane-pyrothionophosphonic acid diamide.

The following examples are given for the purpose of illustrating the preparation of the compounds used in the present invention:

EXAMPLE 1

Preparation of
O-acetyl-N-isopropyl-2-chloroethanephosphonic acid ester amide

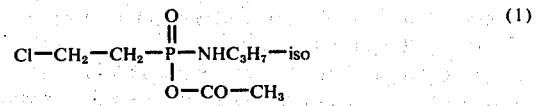

4.1 g (0.05 mole) of dry sodium acetate were added to a solution of 10.2 g (0.05 mole) of N-isopropyl-2-chloroethanephosphonic acid amide chloride in 50 ml of acetonitrile. The mixture was stirred for 5 hours at 50° C and the crystalline precipitate contained in the reaction mixture was then filtered off. The filtrate was concentrated under reduced pressure and the residue was subjected to "slight distillation." This gave 10 g (88% of theory) of O-acetyl-N-isopropyl-2-chloroethane-phosphonic acid ester amide in the form of a colorless oil having a refractive index $n_D^{24}$ of 1.4709.

The compounds listed in Table 1 below were prepared analogously:

Table 1

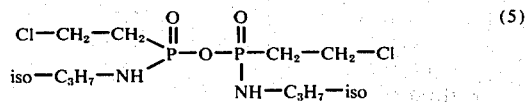

| Example No. | X | R | Physical data (refractive index or melting point) |
|---|---|---|---|
| 2 | O | S‖P(OC$_2$H$_5$)$_2$ | $n_D^{23}$: 1.4816 |
| 3 | O | S‖P(OCH$_3$)(NH$_2$) | $n_D^{23}$: 1.5081 |
| 4 | O | S‖P(OC$_2$H$_5$)(NH—CH$_3$) | M.p. 80° C |

EXAMPLE 5

Preparation of
P,P'-di-isopropylamino-di-2-chloroethanepyrophosphonic acid $$Cl-CH_2-CH_2 \underset{iso-C_3H_7-NH}{\overset{O}{\|}}P-O-\underset{NH-C_3H_7-iso}{\overset{O}{\|}}P-CH_2-CH_2-Cl \quad (5)$$

A mixture of 9 g (0.114 mole) of pyridine, 0.9 g (0.005 mole) of water and 20 ml of methylene chloride was added to a solution of 20.4 g (0.1 mole) of N-isopropyl-2-chloroethanephosphonic acid amide chloride in 50 ml of methylene chloride at 0°–5° C. The reaction solution was stirred for a further 1–2 hours at room temperature and was then extracted with 1 N hydrochloric acid. After drying the organic phase over sodium sulfate, the solvent was stripped off. 12.5 g (70% of theory) of P,P'-diisopropylamino-di-2-chloroethanepyrophosphonic acid diamide were obtained in the form of white crystals of melting point 135° C.

The compound mentioned in Example 6 which follows was prepared analogously.

EXAMPLE 6

Preparation of
P,P'-di-isopropylamino-di-(2-chloroethane)-P,P'-dithiono-pyrophosphonic acid

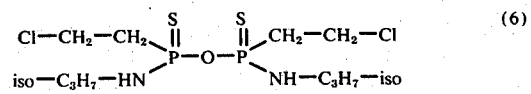

The compound was found to have a refractive index $n_D^{23}$ of 1.4830.

The structures of the compounds of which the preparation is described in Examples 1–6 were in each case demonstrated by IR and NMR spectroscopy.

The active compounds according to the invention affect the physiological metabolism of plant growth and can therefore be used as plant growth regulators.

The diverse actions of the active compounds essentially depend on the point in time at which they are used, relative to the stage of development of the seed or of the plant, and on the concentrations used.

Plant-growth regulators are used for various purposes related to the stage of development of the plant.

The growth of plants can be greatly inhibited with the compounds according to the invention. This inhibition of growth is of interest in grasses, for the purpose of reducing the frequency of cutting grass. An inhibition of vegetative growth is also of great importance in cereals, since lodging can thereby be reduced or completely prevented.

In the case of many crop plants, the inhibition of vegetative growth permits denser planting of the crop, so that a greater yield per area of ground can be achieved. A further mechanism of increasing the yield by means of growth inhibitors is based on the fact that the nutrients benefit blossoming and fruit formation to a greater extent, whilst vegetative growth is restricted.

Promotion of vegetative growth can also be achieved with the compounds according to the invention. This is of great utility if it is the vegetative parts of the plants which are harvested. Promoting the vegetative growth can, however, also simultaneously lead to a promotion of generative growth so that, for example, more fruit, or larger fruit, is formed.

Parthenocarpous fruit can be formed under the influence of the active compounds. Furthermore, the gender of the blossoms can be influenced.

Using the active compounds according to the invention it is also possible favorably to influence the production or efflux of secondary plant materials. The stimulation of latex flow in rubber trees may be mentioned as an example.

During the growth of the plant, lateral branching can also be increased by chemical breaking of the apical dominance. There is interest in this, for example, in the case of plant propagation by cuttings. However, depending on the concentration, it is also possible to inhibit the growth of the side shoots, for example to prevent the formation of side shoots in tobacco plants after decapitation and thus to promote leaf growth.

The influence of the active compounds on the amount of leaf on the plants can be so controlled as to achieve defoliation, for example to facilitate harvesting or to lower the transpiration at a point in time at which the plant is to be transplanted.

Under certain conditions, premature shedding of fruit can be prevented or shedding of fruit assisted in the sense of a chemical thinning out, up to a certain degree. However, assisting the shedding of fruit can also be utilized by carrying out the treatment at harvest time, which facilitates harvesting.

Using the active compounds according to the invention it is furthermore possible to accelerate or delay ripening of fruit and improve the coloring of fruit. Concentrating the ripening of fruit within a certain period of time is also possible. The desired effects can be achieved by varying the concentrations of active compounds used and by application at different times during the development of the plant.

Using the compounds according to the invention, frost resistance and drought resistance can be induced in the plants.

The latent period of seeds or buds of plants, that is to say the endogenic annular rhythm, can be influenced by the active compounds, so that, for example, the plants germinate, shoot or blossom at a time at which they normally show no readiness to do so.

Using the active compounds it is also possible to delay the shooting of buds or the germination of seeds, for example to avoid damage by late frosts in regions where frost is a hazard.

The active compounds according to the present invention can be converted into the usual formulations, such as solutions, emulsions, suspensions, powders, pastes and granulates. These may be produced in known manner for example by mixing the active compounds with extenders, that is, liquid or solid or liquefied gaseous diluents or carriers, optionally with the use of surface-active agents, that is, emulsifying agents and/or dispersing agents and/or foam-forming agents. In this case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds according to the invention can be present in the formulations as a mixture with other active compounds, such as fungicides, insecticides and acaricides.

The formulations in general contain from 0.1 to 95 percent by weight of active compound, preferably from 0.5 to 90 percent by weight.

The active compounds can be used as such, in the form of their formulations or in the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomizing, scattering, dusting and the like.

The active compound concentrations can be varied within a fairly wide range. In general, concentrations of 0.0005 to 2%, preferably of 0.01 to 0.5%, by weight are used.

Further, 0.01 to 50 kg, preferably 0.1 to 10 kg, of active compound are generally used per hectare of soil surface.

The preferred period of time within which the growth regulators are used depends on the climatic and vegetative circumstances.

The compounds according to the invention not only have very good plant-growth-regulating properties but in addition possess herbicidal activity.

The present invention also provides a plant-growth-regulating composition containing as active ingredient a compound of the present invention in admixture with a solid or liquefied gaseous diluent or carrier or in admixture with a liquid diluent or carrier containing a surface-active agent.

The present invention also provides a method of regulating the growth of plants which comprises applying to the plants or a plant habitat a compound of the present invention alone or in the form of a composition containing as active ingredient a compound of the present invention in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

The biotest Examples which follow illustrate the activity of the compounds according to the invention as growth regulators without excluding the possibility of other applications as growth regulators.

EXAMPLE A

Acceleration of ripening/bananas

Solvent: 10 parts by weight of methanol
Emulsifier: 2 parts by weight of polyethylene-sorbitane monolaurate.

To produce an appropriate preparation of active compound, 1 part by weight of active compound was mixed with the stated amounts of solvent and emulsifier and made up to the desired concentration with water.

In each case, 3 unripe bananas were sprayed with 20 ml of the preparation of active compound. The acceleration in ripening in days compared to untreated control fruit was determined.

The active compounds, active-compound concentrations and results can be seen from the table which follows.

Table A

| Acceleration of ripening/bananas | | |
|---|---|---|
| Active compound | Active compound concentration in % | Acceleration of ripening in days |
| $Cl-CH_2-CH_2-\underset{\underset{O-CO-CH_3}{\mid}}{\overset{\overset{O}{\parallel}}{P}}-NHC_3H_7-iso$ (1) | 0.2<br>0.1 | 4<br>4 |
| $\underset{iso-C_3H_7NH}{Cl-CH_2-CH_2}\!\!>\!\!\overset{O}{\overset{\parallel}{P}}-O-\overset{S}{\overset{\parallel}{P}}(OC_2H_5)_2$ (2) | 0.2 | 4 |
| $Cl-CH_2-CH_2-\underset{\underset{OH}{\mid}}{\overset{\overset{O}{\parallel}}{P}}-OH$ (known) | 0.2<br>0.1 | 4<br>3 |
| Water (control) | — | 0 |

EXAMPLE B

Retardation of growth/tomatoes

Solvent: 10 parts by weight of methanol
Emulsifier: 2 parts by weight of polyethylene-sorbitane monolaurate To produce an appropriate preparation of active compound, 1 part by weight of active compound was mixed with the stated amounts of solvent and emulsifier and made up to the desired concentration with water.

Tomato plants about 30 cm high were sprayed with the preparations of active compound until dripping wet. After 10 days, the additional growth was measured and the retardation of growth in % of the additional growth of the control plants was calculated. 100% denotes cessation of growth and 0% denotes a growth which corresponded to that of the untreated control plants.

The active compounds, active compound concentrations and results can be seen from the table which follows.

Table B

| Retardation of growth/tomatoes | | |
|---|---|---|
| Active compound | Active compound concentration in % | Retardation of growth in % |
| Water (control) | — | 0 |
| $Cl-CH_2-CH_2-\underset{\underset{OH}{\mid}}{\overset{\overset{O}{\parallel}}{P}}-OH$ (known) | 0.2<br>0.1 | 40<br>35 |

Table B-continued

Retardation of growth/tomatoes

| Active compound | Active compound concentration in % | Retardation of growth in % |
|---|---|---|
| $Cl-CH_2-CH_2$ \ $P$ (=O)(=S)$-O-P(OC_2H_5)_2$ / $iso-C_3H_7-NH$ (2) | 0.2 | 80 |
| $Cl-CH_2-CH_2$ \ $P$ (=S)(=S)$-O-P$ (-$CH_2-CH_2-Cl$)(-$NH-C_3H_7-iso$) / $iso-C_3H_7-NH$ (6) | 0.2 | 55 |
| $Cl-CH_2-CH_2$ \ $P$ (=O)(=S)$-O-P$ (-$OC_2H_5$)(-$NH-CH_3$) / $iso-C_3H_7NH$ (4) | 0.2 / 0.1 | 80 / 40 |
| $Cl-CH_2-CH_2$ \ $P$ (=O)(=O)$-O-P$ (-$CH_2-CH_2-Cl$)(-$NH-C_3H_7-iso$) / $iso-C_3H_7-NH$ (5) | 0.2 / 0.1 | 90 / 55 |

EXAMPLE C

Retardation of growth/beans

Solvent: 10 parts by weight of methanol
Emulsifier: 2 parts by weight of polyethylene-sorbitane monolaurate To produce an appropriate preparation of active compound, 1 part by weight of active compound was mixed with the stated amounts of solvent and emulsifier and made up to the desired concentration with water.

Young bean plants about 10 cm high were sprayed with the preparation of active compound until dripping wet. After 14 days, the additional growth was measured and the retardation of growth in % of the additional growth of the control plants was calculated. 100% denotes cessation of growth and 0% denotes a growth which corresponded to that of the untreated control plants.

The active compounds, active-compound concentrations and results can be seen from the table which follows.

Table C

Retardation of growth/beans

| Active compound | Active compound concentration in % | Retardation of growth in % |
|---|---|---|
| Water (control) | — | 0 |
| $Cl-CH_2-CH_2-P$(=O)(-OH)(-OH) (known) | 0.05 | 40 |
| $Cl-CH_2-CH_2$ \ $P$(=O)(=S)$-O-P(OC_2H_5)_2$ / $iso-C_3H_7NH$ (2) | 0.05 | 70 |
| $Cl-CH_2-CH_2-P$(=O)(-$NHC_3H_7-iso$)(-$O-CO-CH_3$) (1) | 0.05 | 70 |
| $Cl-CH_2-CH_2$ \ $P$(=O)(=S)$-O-P$(-$OC_2H_5$)(-$NH-CH_3$) / $iso-C_3H_7-NH$ (4) | 0.05 | 65 |

It will be appreciated that the instant specification and examples are set forth by way of illustration and not limitation, and that various modifications and changes may be made without departing from the spirit and scope of the present invention.

What is claimed is:

1. N-isopropyl-2-chloroethane-(thionó)-phosphonic acid ester amide compounds of the general formula:

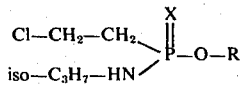 (I)

wherein
X is oxygen or sulfur, and
R is acetyl or a group of the formula

wherein
X' is oxygen or sulfur,
R' is alkoxy of from 1 to 4 carbon atoms or 2-chloroethyl, and
R'' is alkoxy or alkylamino of up to 4 carbon atoms or an $NH_2$— group.

2. N-isopropyl-2-chloroethane-phosphonic acid ester amide compounds as claimed in claim 1 wherein X is oxygen.

3. N-isopropyl-2-chloroethane-(thiono)-phosphonic acid ester amide compounds as claimed in claim 1 wherein X is sulfur.

4. N-isopropyl-2-chloroethane-(thiono)-phosphonic acid ester amide compounds as claimed in claim 1 wherein R is acetyl.

5. N-isopropyl-2-chloroethane-(thiono)-phosphonic acid ester amide compounds as claimed in claim 1 wherein R is

6. N-isopropyl-2-chloroethane-(thiono)-phosphonic acid ester amide compounds as claimed in claim 5 wherein R' is alkoxy of up to 4 carbon atoms.

7. N-isopropyl-2-chloroethane-(thiono)-phosphonic acid ester amide compounds as claimed in claim 5 wherein R' is 2-chloroethyl.

8. N-isopropyl-2-chloroethane-(thiono)-phosphonic acid ester amide compounds as claimed in claim 5 wherein R'' is alkoxy of up to 4 carbon atoms.

9. N-isopropyl-2-chloroethane-(thiono)-phosphonic acid ester amide compounds as claimed in claim 5 wherein R'' is alkylamino of up to 4 carbon atoms.

10. N-isopropyl-2-chloroethane-(thiono)-phosphonic acid ester amide compounds as claimed in claim 5 wherein R'' is an $NH_2$— group.

11. N-isopropyl-2-chloroethane-(thiono)-phosphonic acid ester amide compound as claimed in claim 1 designated O-acetyl-N-isopropyl-2-chloroethane-phosphonic acid ester amide.

12. N-isopropyl-2-chloroethane-(thiono)-phosphonic acid ester amide compound as claimed in claim 1 designated P-(isopropylamino-2-chloroethane)-P'-(diethoxy-P'-thiono)-pyrophosphonic acid.

13. N-isopropyl-2-chloroethane-(thiono)-phosphonic acid ester amide compound as claimed in claim 1 designated P-(isopropylamino-2-chloroethane)-P'-(methoxy-amino)-P'-thionopyrophosphonic acid.

14. N-isopropyl-2-chloroethane-(thiono)-phosphonic acid ester amide compound as claimed in claim 1 designated P-(isopropylamino-2-chloroethane)-P'-(ethoxy-methylamino)-thionopyrophosphonic acid.

15. N-isopropyl-2-chloroethane-(thiono)-phosphonic acid ester amide compound as claimed in claim 1 designated P,P'-diisopropylamino-di-2-chloroethanepyrophosphonic acid.

16. N-isopropyl-2-chloroethane-(thiono)-phosphonic acid ester amide compound as claimed in claim 1 designated P,P'-diisopropylamino-di-(2-chloroethane)-P,P'-dithiono-pyrophosphonic acid.

17. Plant growth regulant compositions comprising an agriculturally acceptable carrier and, in effective amounts, an N-isopropyl-2-chloroethane-(thiono)-phosphonic acid ester amide compound as claimed in claim 1.

18. Method of influencing the growth of plants, which method comprises applying to the plants or their habitat an effective amount of an N-isopropyl-2-chloroethane-(thiono)-phosphonic acid ester amide compound of the general formula:

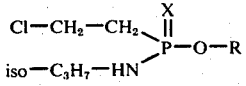 (I)

wherein
X is oxygen or sulfur, and
R is acetyl or a group of the formula

wherein
X' is oxygen or sulfur,
R' is alkoxy of from 1 to 4 carbon atoms or 2-chloroethyl, and
R'' is alkoxy or alkylamino of up to 4 carbon atoms or an $NH_2$— group.

19. Method as claimed in claim 18 wherein the growth of plants is enhanced.

20. Method as claimed in claim 18 wherein the growth of plants is inhibited.

21. Method as claimed in claim 18 wherein the growth of plants is altered.

22. Method as claimed in claim 18 wherein said compound is selected from the group consisting of:
O-acetyl-N-isopropyl-2-chloroethane-phosphonic acid ester amide;
P-(isopropylamino-2-chloroethane)-P'-(diethoxy-P'-thiono)-pyrophosphonic acid;
P-(isopropylamino-2-chloroethane)-P'-(methoxyamino)-P'-thionopyrophosphonic acid;
P-(isopropylamino-2-chloroethane)-P'-(ethoxymethyl amino)-thionopyrophosphonic acid;
P,P'-di-isopropylamino-di-2-chloro-ethanepyrophosphonic acid; and
P,P'-di-isopropylamino-di-(2-chloroethane)-P,P'-dithiono-pyrophosphonic acid.

* * * * *